United States Patent [19]

Kirkland

[11] Patent Number: 4,492,111

[45] Date of Patent: Jan. 8, 1985

[54] RHEOLOGICAL PENETROMETER

[76] Inventor: James L. Kirkland, 2211 Lombardy Ave., Panama City, Fla. 32405

[21] Appl. No.: 309,403

[22] Filed: Oct. 7, 1981

[51] Int. Cl.³ .............................................. G01N 3/00
[52] U.S. Cl. .......................................... 73/84; 75/85; 75/9; 324/323
[58] Field of Search ............... 73/84, 85, 8 L, 170 A, 73/9; 324/323

[56] References Cited

U.S. PATENT DOCUMENTS

| 3,298,222 | 1/1967 | Costello et al. | 73/84 |
| 3,339,404 | 9/1967 | Brooks et al. | 73/84 |
| 3,623,359 | 11/1971 | Paine | 73/84 |
| 3,690,166 | 9/1972 | Grice | 73/84 |
| 3,906,781 | 9/1975 | Vlasblum | 73/84 |
| 4,197,737 | 4/1980 | Pittman | 73/178 R |

*Primary Examiner*—Anthony V. Ciarlante
*Attorney, Agent, or Firm*—Cushman, Darby & Cushman

[57] ABSTRACT

A free falling or projectable penetrometer for simultaneously determining a multiplicity of ground characteristics during penetration and retracking cycles and while at rest following full penetration. The apparatus employs a multitude of sensing elements and is further characterized by the presence of at least three electrode pairs one aligned with the central axis of the penetrometer with the other two pairs being positioned orthogonally in a common plane that is itself perpendicular to the central axis. An onboard power supply is included together with telemetry equipment to generate ground characteristics and transmit such signals.

13 Claims, 18 Drawing Figures

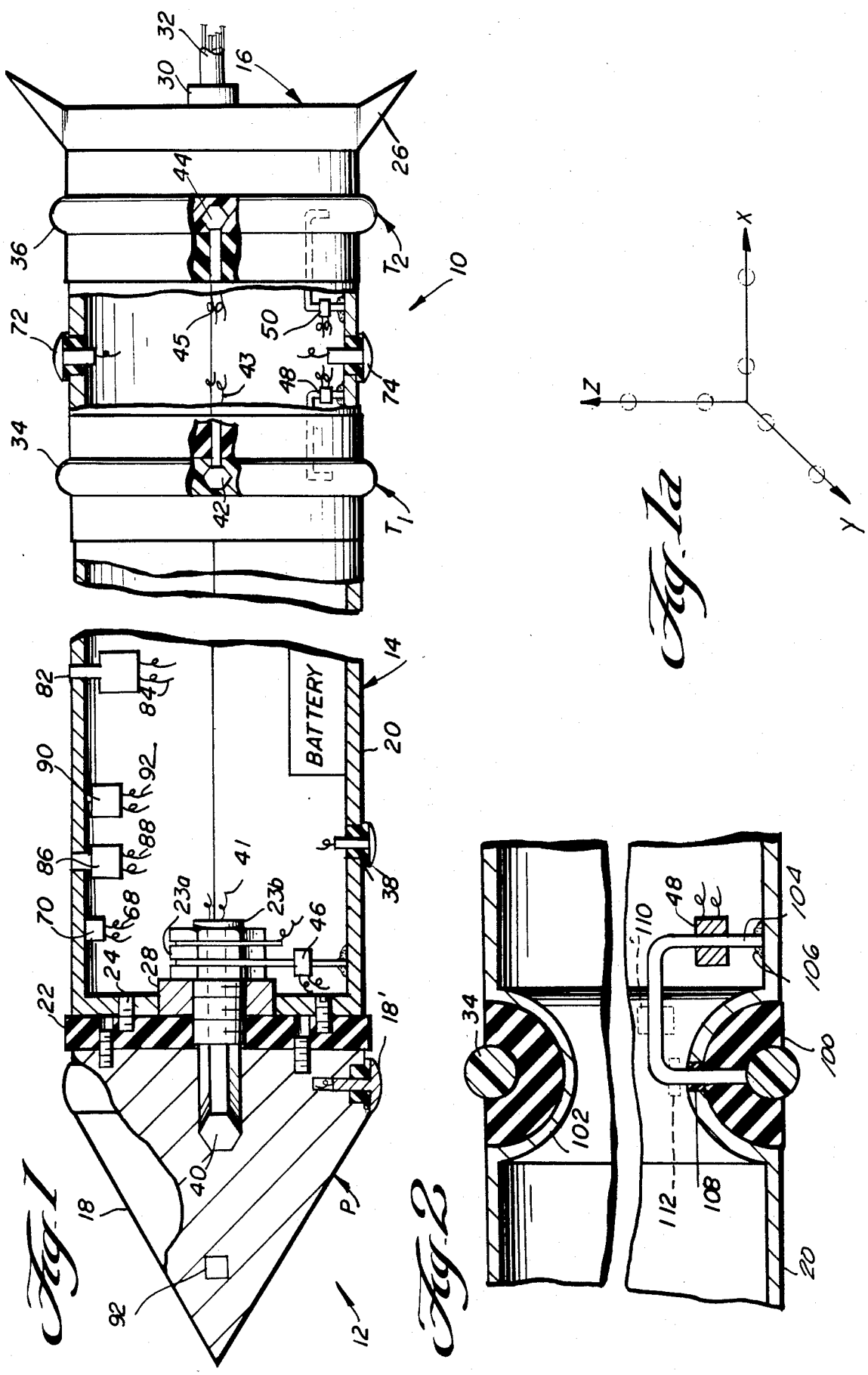

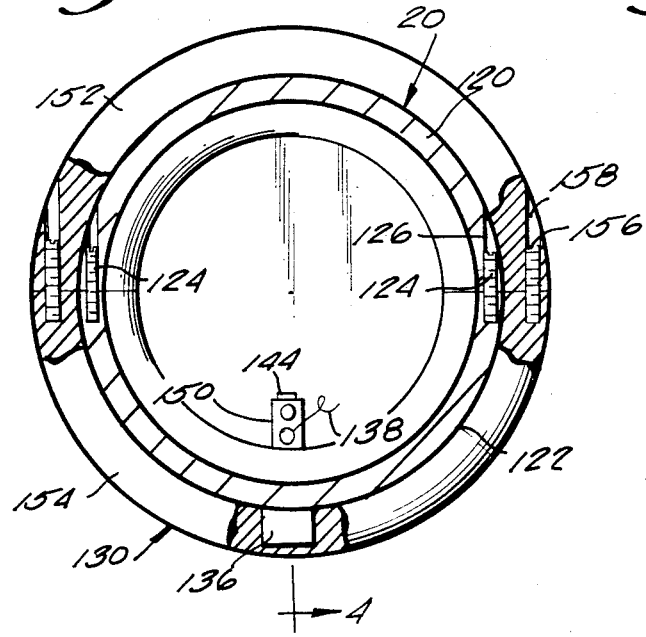
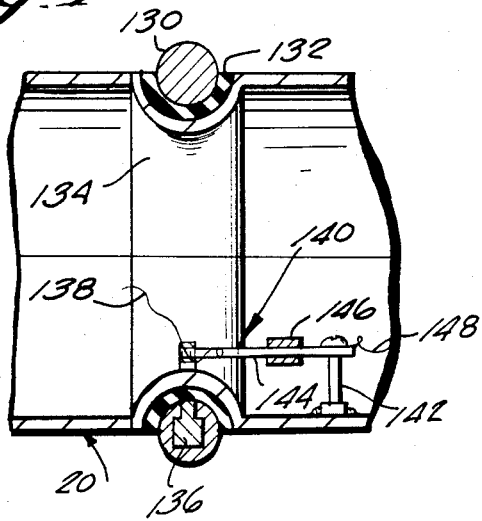
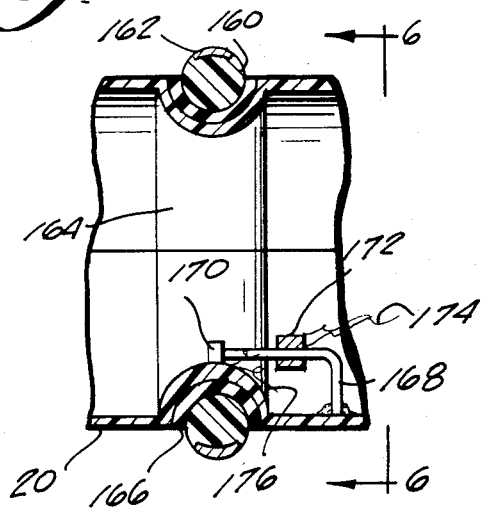
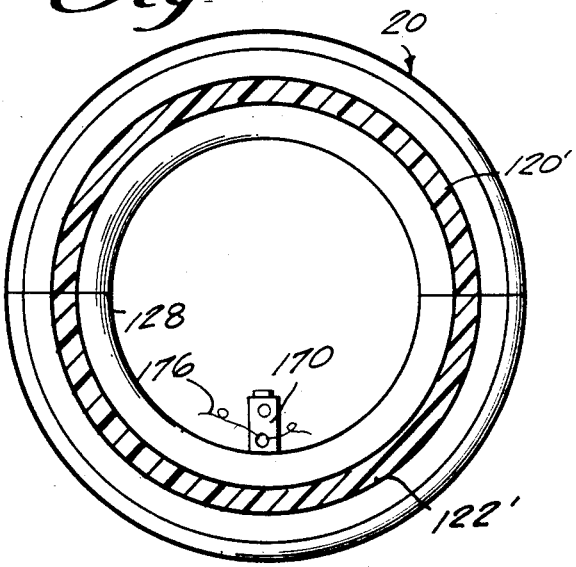

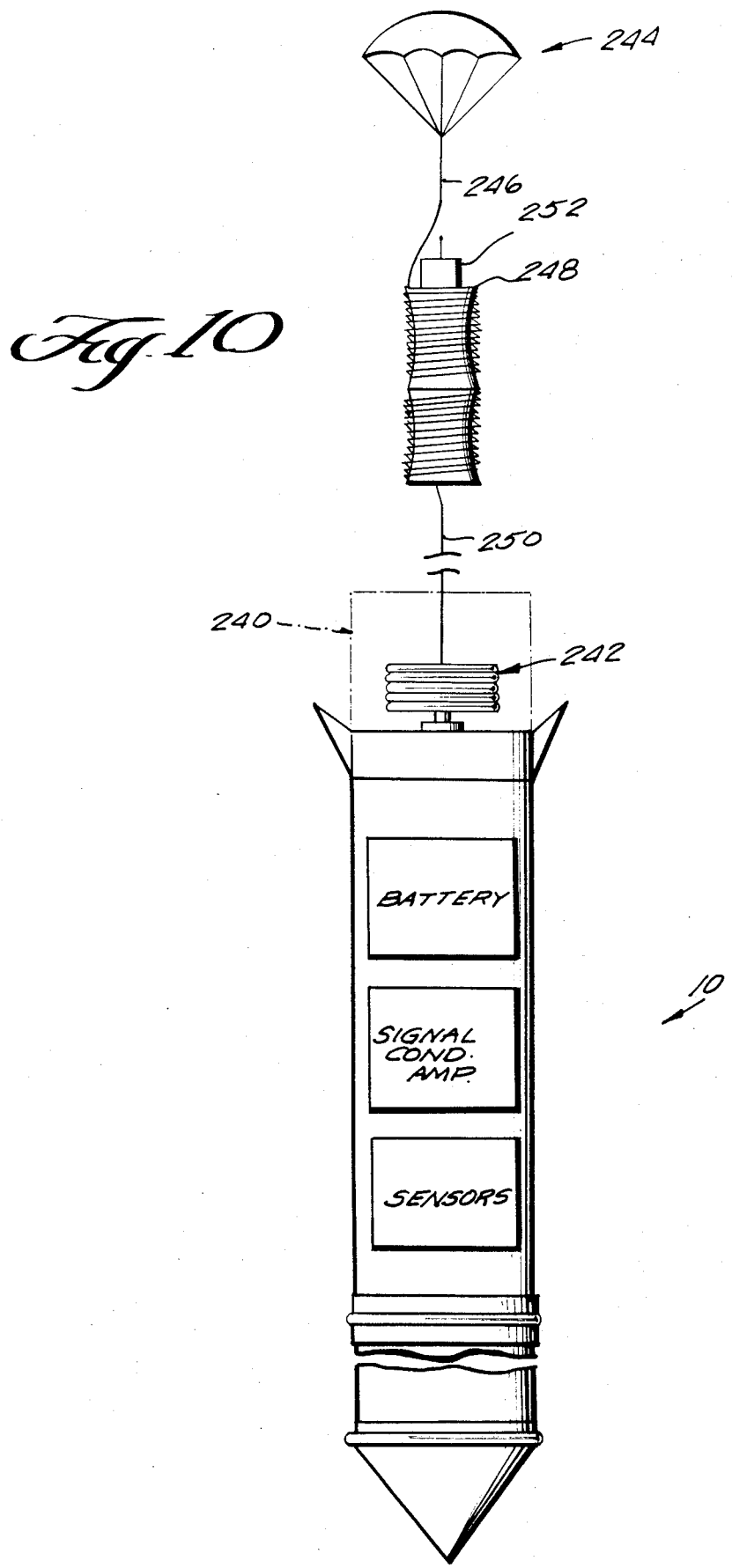

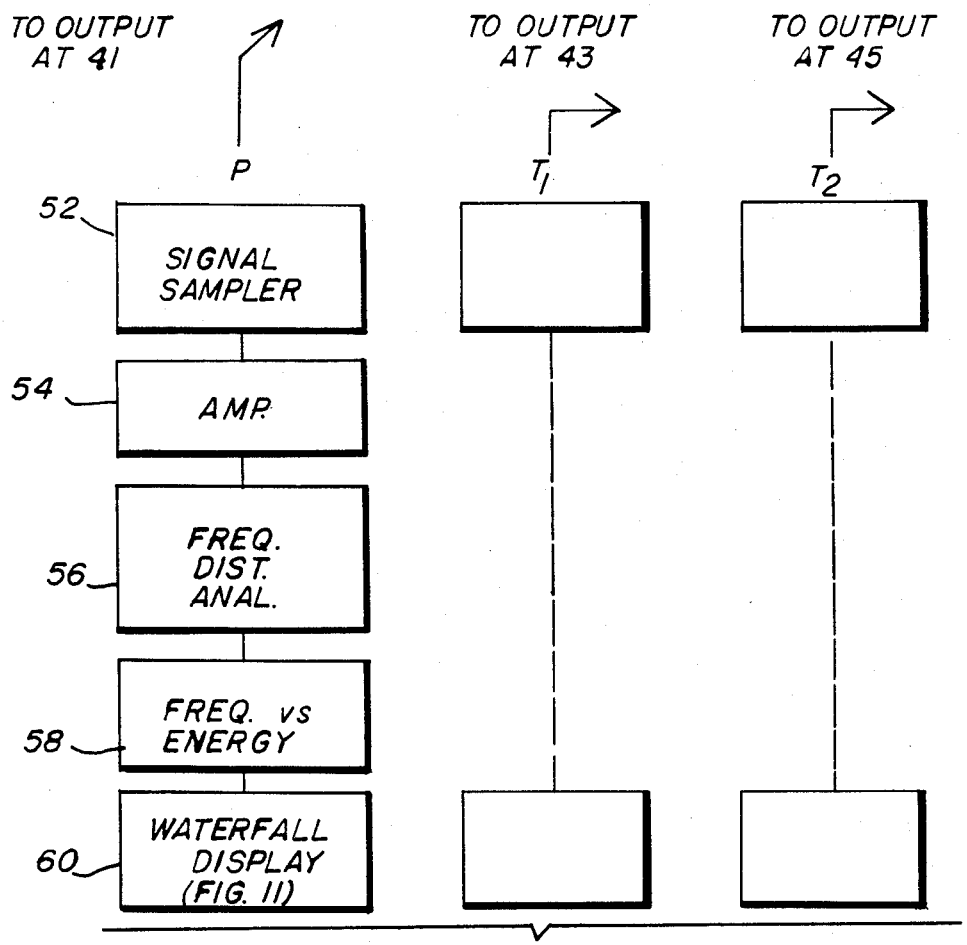
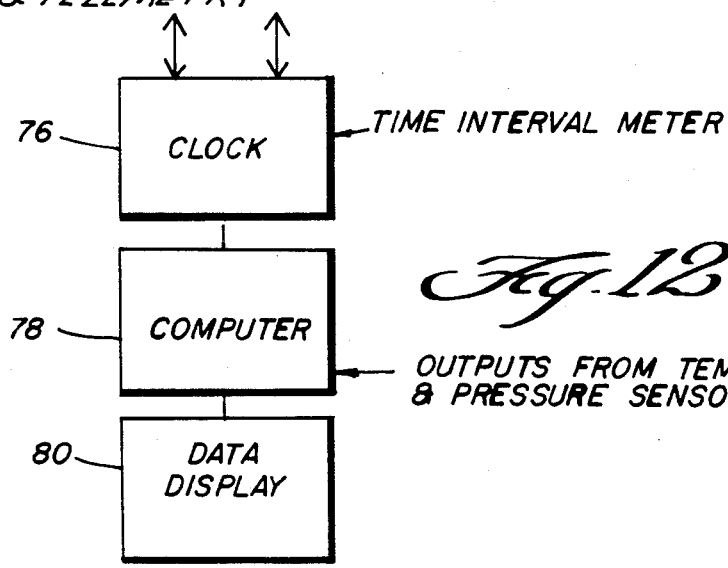

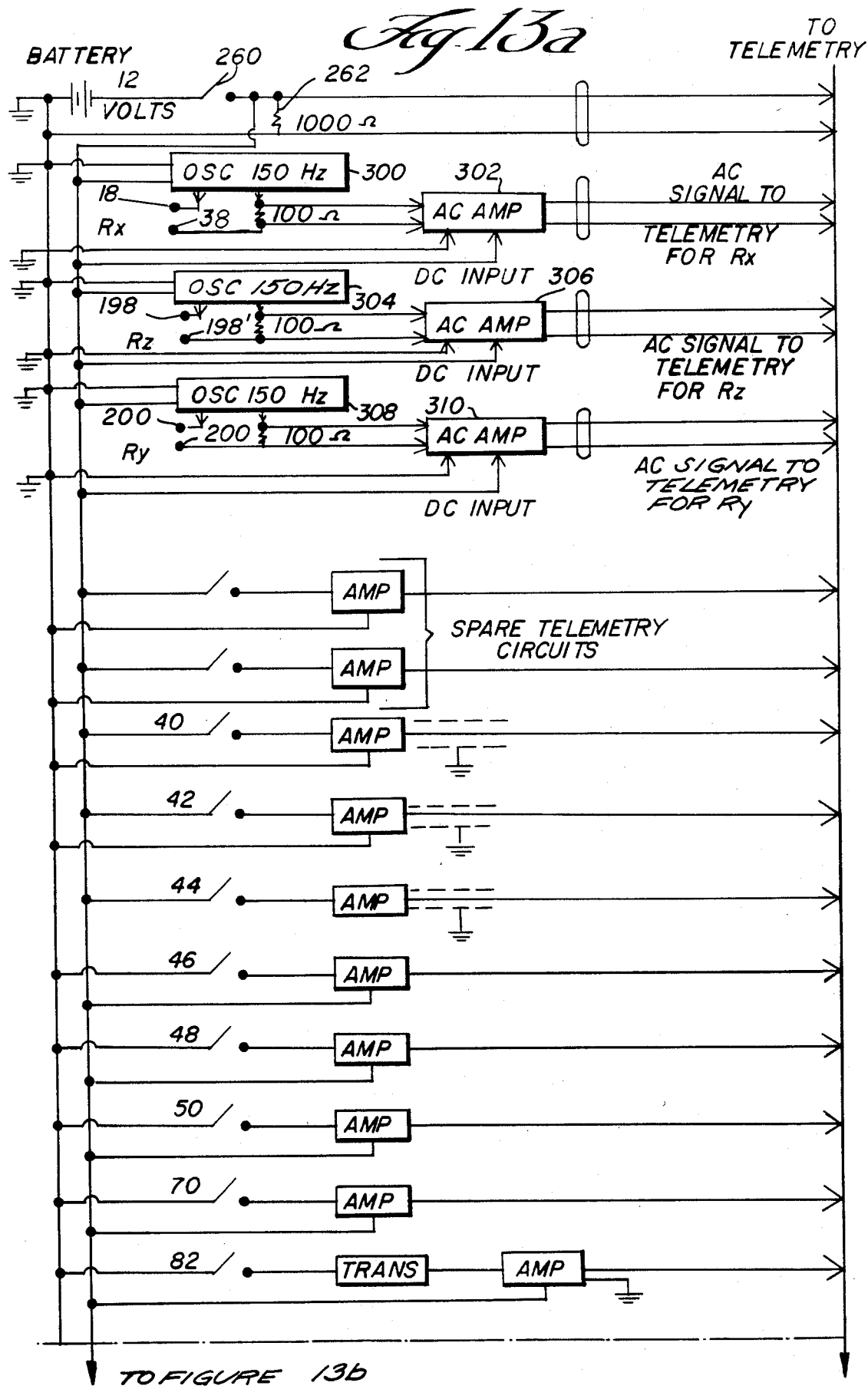

RHEOLOGICAL PENETROMETER

FIELD OF THE INVENTION

This invention relates to penetrometers or generally to probe apparatus for use in determining a wide variety of characteristics of various types of media including ground conditions such as soil or water and other various fluids or liquids which may be examined or tested by the apparatus.

BACKGROUND OF THE PRESENT INVENTION

In recent years, it has often been found desirable, indeed sometimes necessary, to obtain some type of indication as to the characteristics of ground, soil or underwater soil conditions including the rigidity, compaction or load bearing characteristics of such surfaces prior to initiating any one of a variety of types of operations on that surface. This becomes more of a concern when large areas need to be the basis of such operations or where foliage and surface growth prohibit easy or ready investigation of such surfaces by aerial means. Where there is no surface vegetation, aerial surveys may provide a sufficient degree of information for some types of operations. Likewise, where a relatively small area needs to be investigated, that can be done by simply having individuals move through the area and make on site investigations. In many other instances, however, on site or aerial means and some other means has to be found. Remote and otherwise inaccessible areas including both land and sea or river bottoms can only be effectively studied through more sosphisticated techniques. At other times it is desirable to determine what is flowing within closed prior art conduits.

Examples of such technqiues include Costello, et al, U.S. Pat. No. 3,298,222, Brooks, et al, U.S. Pat. No. 3,339,404, Payne, U.S. Pat. No. 3,623,359, Grice, U.S. Pat. No. 3,690,166, Vlasblom, U.S. Pat. No. 3,906,781 and Thompson, U.S. Pat. No. 4,007,633.

In Costello et al, the device is one that is used from a ship and allowed to be passed down through water at a constant velocity for impacting the bottom of a water course. An accelerometer or, a signal generating system, is connected by means of a cable directly connected to the ship and vehicle deceleration is monitored the results of which indicate the load bearing characteristics of the bottom surface.

Brooks et al was designed as a device for measuring and transmitting impact accelerations on the moon's surface. Impact acceleration data is compared with known acceleration time histories to determine physical properties of the soil being inspected including surface hardness, bearing strength and penetrability of the body. Brooks et al accomplishes this task by firing off individual penetrometers, the outputs from which are transmitted back to a receiving station on Earth.

Payne relates to a penetrometer also suited for use in determining the load characteristics of the lunar surface. The device was connected to the bottom of the lunar module itself; displacement of a pad member forced against the surface was measured over a given period of time to determine the capacity of the soil to support vertical loads. In particular, the probe included an improved pad structure that allowed that pad to be laterally displaced so that both vertical and lateral displacements could be detected and measured to determine the load bearing characteristics of the soil.

In Grice, an instrument platform was positioned on the bottom of a body of water and a device which burrowed its way into the soil was lowered into place and formed a passageway through which it moved. While various readings are taken with respect to conditions along the bore hole, it is not a penetrometer designed to make readings as it passes vertically through the soil or area being examined on the basis of a free fall drop.

Vlasblom discloses a soil probe or penetrometer designed to be pressed into soil that includes an annular, elastically deformable wall portion. Strain gauges are mounted on the interior surface thereof to sense pressure acting transversely to the axis of the tube. A water pressure gauge is also included and intergranular soil pressure is determined from the difference between the two pressures. In addition, there is an indication that insulated annular electrodes can be included for determining the electrical conductivity of the surrounding soil so that soil density information can derived. However, no further description is included and there is no structure set forth for accomplishing such a result.

Thompson is somewhat similar to Costello et al in that it is a device which is allowed to pass through water or the ocean until it strikes and imbeds itself in the ocean bottom to detect physical characteristics of the sea floor. However, rather than using a cable, the invention makes use of an acoustic signal which is transformed into an appropriate electrical analog signal with the data being sent from the penetrometer thus presenting a different way for transmitting signals from the penetrometer with respect to its deceleration as it comes to rest in the sea floor.

While the foregoing references describe various attempts in designing penetrometers, none are capable of producing a wide variety of measurements simultaneously to permit a number of determinations of soil characteristics beyond that connected with rigidity, compaction or load bearing characteristics or simple measurements indicating the presence or absence of water. Likewise, none are concerned with determining electrical resistance measurements in three orthogonal directions, determining stratification information, or measuring the depth of various mediums throughwhich the penetrometer passes. Additionally, none can distinguish between Newtonian and non-Newtonian fluids nor determine characteristics concerning the grains constituting the medium through which the penetrometer passes and comes to rest.

Further, the prior art has not recognized the desirability to track and retrack through the medium.

SUMMARY OF THE PRESENT INVENTION

In the present invention, the disadvantages of the prior art instruments and apparatus have been avoided by designing an apparatus which provides mechanisms for measuring rheological and other properties as well as electrical resistance and resistivity of materials, and/or acoustic monitoring simultaneously or independently, with means for defining the spatial location of these points of measurement in the medium. This measurement is accomplished by means of bodies making contact with the medium and moving along a predetermined path relative to the medium followed by the retracking of other bodies along substantially the same predetermined path.

Travel of the apparatus through Newtonian materials produces a characteristic result that will be repeated in subsequent passes or during retracking. Travel of the apparatus through non-Newtonian material produces initial penetration characteristics associated with the penetrating point and separate and distinctive re-tracking characteristics. The "penetration" cycle and the "re-track" cycle are not equal and the frequencies of the "penetration" and "re-track" responses are likewise not equal. This is due to the penetration body leaving a path or "track" by disturbing the medium on its original penetration movement as created by the nose of the penetrometer. This disturbance of the medium or the track thus created has different drag characteristics from the undisturbed material ahead of the penetrometer, hence the characteristics of movement in this previously created track are different.

The signatures or movement characteristics of the device through a non-Newtonian material containing grains of various sizes and intergranular forces will result in producing a high-frequency modulation superimposed on a low frequency signal as small, nearly uniform-size grains are encountered, whereas large jagged spikes will be produced as much larger anomalies are encountered with these spikes being modulated by the subsequent interparticle noises resulting from large particle movmement and their interaction with smaller particles. An example of such a material would be a clay and water slurry (providing the basic "carrier frequency") containing some "three millimeter diameter" soil particles (providing the high-frequency modulation of this "carrier frequency") and some "twenty to thirty millimeter diameter" fragments (which in the process of being pushed aside by the penetrating body, in turn move a number of smaller particles thereby creating the interparticle noises which are transmitted to the sensing elements). By starting with a smooth clay and water slurry, which may be Newtonian, and by adding incrementally the other grains and obtaining and analyzing the frequency spectra thus generated, one may generate a "catalog" of responses versus materials and their ratios in a mixture. The same cataloging can be done, as well, with other media. Thus, it is possible to identify characteristics including grain size, shape and orientation, the packing density of the grains as well as the packing geometry separate layers and the presence or absence of materials. In the case of a dielectric material imbedded in an electrical conductor, the relative amounts of each may be determined. Furthermore, if the dielectric material is capable of exhibiting a preferred direction in which it conducts, directs or guides electricity, this direction may be measured and characterized in terms of a resistance or resistivity, or its reciprocal vector. These data may be used to determine grain size, void size, grain roundness, grain sphericity, or other particle shapes.

Power requirements can also be calculated for various soil conditions and is a function of the extent of the penetration (distance) over a given period of time.

The bodies, which move with respect to the medium, may have a variety of suitable shapes and their vibration may be monitored by suitable transducers mounted directly on, within, or adjacent sensing bodies on the penetrometer, or in communication with such bodies by fluid or mechanical coupling techniques or through electrical induction, optical techniques in the form of a coherent light (laser) or polarized light, acoustic or other direct, radiative or inductive methods. Separate monitoring means, external to the body, may thus monitor the vibrations of the bodies or the resulting perturbations in the medium or both, simultaneously or sequentially.

It may be shown experimentally that a single body moving through a medium will cause a perturbation in the medium and a vibration of the body. This periodicity of wakes is well-known and may be characterized in terms of the Reynolds number of the body.

This applies generally to motion of the body in purely viscous materials such as oil or water, which materials are defined by a "viscosity coefficient" or simply "absolute" or "dynamic" viscosity, which terminology is universally used and understood by those skilled in viscosity and consistency measurements. Some suspensions of solids in liquids may behave as purely viscous materials. A dilute suspension behaving as a Newtonian fluid, or a pure Newtonian fluid such as water, will cause a body in relative motion with it to vibrate at a frequency which we define as $f_1$. Some compensation in $f_1$ may be required due to variations in temperature, pressure, etc., but these can be obtained experimentally. These purely Newtonian materials have no structure which can be disturbed by passage of a body which would cause the material to have a "memory".

Typical non-Newtonian materials have structures which do exhibit a "memory". When a body penetrates certain of these materials, for example, grease, or heavy suspension a visible track often results. Simultaneously, during this penetration phase a vibration frequency $f_1$ will result due to drag related to the Reynolds number.

These non-Newtonian materials do have a structure which is disturbed by the passage of a body and which may exhibit a "healing time" depending upon the nature of the material and the degree to which the structure is disturbed. If a second (or third or more) body is now constrained to follow the first body on the identical or nearby path through the material, it will experience a drag that is different from that of the initial penetrating body, and each subsequent body will generate a different frequency, or frequencies. A comparison of the frequencies generated by the separate bodies yields useful information about the material. These parameters may be obtained experimentally as previously mentioned.

I define the frequencies associated with this technique as follows:

$f_1$—the basic penetration or "track" frequency derived from the period of the body for a given material, driving force, temperature.

$f_2$—the "re-track" frequency for a material under the same conditions as "track".

$f_3$—all other frequencies present in a "track" or "re-track" test. These most commonly are the "scraping" or frictional signals generated by contact of the penetrating body with the medium, intergranular signals generated by relatively small grains passing by in contact with each other as the penetrating body forces them out of the way, signals generated when the penetrating body encounters grains large enough to present very high penetration resistance as they are moved aside and, while being moved aside, and signals generated as the large grains encounter smaller grains which in turn generate interparticle signals.

These frequencies may exhibit preferred portions of the spectrum depending on the shape and size of the penetrator, its speed and direction in the medium, the particle size and distribution of the particles in the medium, the angularity of the particles, the geometry of the stacking of the individual particles with respect to each other, and other factors. The characteristics of power versus frequency for $f_3$ signals may be obtained experimentally and cataloged for various materials and their internal structures. When the materials are soils in water, such soil parameters as moisture content, void ratio, grain size and distribution and soil type may be correlated with $f_1$, $f_2$ and particularly $f_3$. This is very important in cases where a soil has been deposited in a preferred grain orientation and will exhibit different shear strengths in different directions due to the grain orientation.

Some non-Newtonian materials may "heal" to some extent in the time between "track" and "re-track" penetrations. This phenomenon may be useful in identifying materials and may also be observed experimentally and cataloged.

It is possible to relate these drag and shear effects and interparticle forces to the electrical resistivity of a medium, such electrical resistivity effects providing further useful information about the medium being penetrated by the body or bodies. The device can be equipped with contacts to measure electrical resistance which can be sensed and transmitted and I prefer to measure electrical resistance in those separate, orthogonal directions. These grain orientations also give rise to "directional resistance" signals which are useful in differentiating, for example, a clay deposit in the dispersed state (large number of grains oriented parallel to each other), the flocculated state (large number of grains randomly oriented), or the re-molded state (some state of grain orientation somewhere between dispersed and flocculated).

Electrically conductive Newtonian materials normally exhibit uniform electrical resistivity in all directions, for example, salt water. However, certain non-conductive suspensions in this same electrolyte will very likely cause it to behave as a non-Newtonian material rheologically while simultaneously causing it to exhibit directional resistivity. This effect is also commonly observed in rocks; the electrical resistivity of the rock depends on the direction of the electric current with respect to the arrangement of the particles. The particle arrangement constrains the electric current to follow the electrolytic path between the grains or particles. Such a material is called anisotropic. (Geophysical Exploration, C. A. Heiland, Prentice-Hall, Inc., N.Y., 1940). Typical grain arrangements are spheres in cubic, rhombic or hexagonal arrangement, often found in stratified deposits not necessarily rocks. The shear strength of such a material can vary directionally depending on the spatial arrangement of the grains, for example, in a sediment or a sludge. By performing directional resistance measurements in a material while simultaneously examining its rheological characteristics in a variety of directions, the combined knowledge of these two parameters with their spatial location, can lead to a better and more useful understanding of the medium.

These two techniques, drag measurement with perturbations, and directional resistance, complement each other. For example, in some instances the force available to drive the bodies in a very thick medium may be so small as to be unable to obtain $f_2$ above the noise level of the apparatus whereas $f_1$ and $f_3$ are measurable. These latter signals, when utilized with the electrical conductivity signals, will form the basis for understanding the nature of the material even though some of the perturbation signals are absent. If the perturbation signals from the moving bodies show all or some of the characteristics of a body moving in a Newtonian or a non-Newtonian medium, but the directional R signatures are absent, one may conclude that the directional R measurement is being performed in an electrolyte of extremely high resistivity, for example, oil. This provides additional information for classifying the material.

Finally, the electrical conductivity features provide additional useful information about the motion of the device in the medium being examined. For example, if the device is a linear array of perturbing bodies and electrodes being forced, by gravity for example, into an electrically-conductive medium, the velocity and deceleration of the body in this medium, and its depth, may be obtained by monitoring the sequence of electrode actuations as the device enters the medium. Simultaneously, if there is a spatial gradient in the electrical conductivity of the medium, as for soil or as may be occasioned by a "wedge" of salt water, this would be located by monitoring the electrical conductivity from the surface to the point where the device stops penetrating through the use of electrode pairs grouped to measure resistance, R, in three directions, one pair along the axis of the device and two pairs horizontally with these latter two pairs being preferably in a plane located orthogonally to that axis at a known position and with the electrode pairs arranged 90 degrees from one another or at separate but known locations along the length of the penetrometer. For these horizontal electrode pair positions, the electrodes in each pair should preferably be directly opposite one another on the body of the penetrometer. Thus, measurements can be made in X, Y and Z directions.

A penetrator can be equipped to perform these measurements by using an electrode-pair measuring resistance along the X-axis which is positioned along the main central axis of the penetrometer and in two other directions, Z and Y, preferably located in a plane perpendicular to the X-axis with separate electrode-pairs for measuring resistance (R) in the Z direction and in the Y direction. The electrodes in each pair are preferably diametrically opposed so that proper readings across the diameter of the pentrometer can be taken. These electrode-pairs operate as a sequence of electrical switches as well and deliver timed actuations from which velocity and acceleration data may be derived.

Another useful application of this technique using linear arrays of perturbing bodies with electrodes is for examining soil structures, for example, from the surface downward, possibly terminating at the water table. Thus, included on the penetrometer are electrode-pairs spaced or located at regular intervals along the penetrometer. The pairs occur in triads with one pair of electrodes "looking" in the X-direction, another pair "looking" in the Y-direction, and a third pair "looking" in the Z-direction. Not only will these triads examine the resistance along X-Y-Z continuously as the penetrometer penetrates giving an instantaneous response, they will also provide a resistance response versus time after the penetrometer has come to rest.

The volume of the penetrometer as it penetrates the earth, will suddenly displace an equal volume of material. This volume of material will move in variety of ways and the form of the initial movement and the type of subsequent activity can be monitored to produce additional characteristic responses of soil or ground conditions. During penetration, the penetrometer will have compacted the gas in between the grains and likewise collapsed the pore structure or the spaces in between grains and in the process expell water that had been held in those pores. This may produce a radical change in soil resistance and resistivity in the volume surrounding the penetrometer as there is now more water (electrolyte) available in this compacted volume than immediately theretofore. Consequently, resistivity would expectedly decrease in this immediate volume. Therefore, the nose electrodes will monitor resistivity immediately after penetration, and the following electrodes will monitor this same volume sometime later depending on how fast the penetrometer is penetrating the soil or other material. When the penetrometer stops, the electrodes will continue to measure R in the three directions, X, Y and Z. With the passage of time, the compressed gases and solid grains tend to redistribute the incompressible water outwardly through an additional volume of material beyond the "initial compression zone". As this redistribution occurs over time, the resistance measured will go up because there is less water (electrolyte) per unit volume of material, and the electrolyte is basically the only conductor of electricity in this total volume. There is a limit on the voltage applied to the electrode pairs and the probe will be able to "see" only so far outwardly into the soil, and examine only a given volume even if the soil is completely saturated with electrolyte. Likewise, the initial impact and penetration may have caused the water in the compound volume to be quickly and initially moved way and over a period of time the ground water may return. Thus, both this redistribution and pulsing of moisture can be observed.

Certain porous and permeable soils (e.g. sands) can redistribute this water rapidly; others cannot (e.g. clay). Also, some soils may be stratified and be more permeable in some directions than in others. Therefore, if each directional $R_x$, $R_y$ and $R_z$ is monitored for its change with time, changes in the magnitude and direction of the vector sum of these conditions allow computation of:

(a) degree of saturation;
(b) direction of major flow of water, i.e., direction of major permeability path;
(c) pore pressure; and
(d) soil type Correlation of this "R versus time" curve with "deceleration versus depth" allow the various strata, their depth, permeabilities, etc. to be defined.

Such a simultaneous examination of the electrical resistance and drag signals can provide useful information about the moisture gradient and soil structure from surface to the depth penetrated which in turn may be interpreted in terms of shear strength for mechanical engineering purposes or to assess the permeability of soil for fertilizers for agricultural purposes. Numerous other practical applications for the device will become obvious as the capabilities and features of the device are described.

Still another application of the present invention is in detecting "grain alignment". Spaces between grains are permeated by an electrically-conductive medium. The directional resistance effect is pronounced when the difference in electrical conductivity between the material of the grain and the permeating medium is great. The permeating medium is the electrolyte. Two general classes of grain exist: (1) those which are essentially solid and have no cracks, fissures or conduits that may contain electrolyte (Sands are largely like this.); and (2) those which have a "platelet" structure which are capable of containing sheets of water between the platelets, such sheets being several watermolecules thick (These are the clay minerals principally kaolinite, illite, and montmorillonite, and usually have a net negative charge on the surface due to their molecular structure.).

Thus, each grain has associated with it, an electrically conductive material such as water comprising an electrical resistor, and in an orderly arrangement, for example deposition by an electric field. These resistors are connected in series or in parallel or in combinations (series-parallel) in a three-dimensional matrix to provide a path having certain electrical resistance and resistivity characteristics which can be recognized and associated with that structure. As certain mechanical properties accompany these grain arrangements, a knowledge of the electrical resistance directionally may lead to a knowledge of the mechanial properties referred to heretofore.

Sand grains usually are very nearly solid and have no pronounced natural surface electrical charge like clays. Their shape is generally measured by reference to a coefficient of sphericity, having no classification by long, medium or short axes. However, it has been observed that sand grains in channels are often oriented in the direction of flow. Sand grains pack as if they were oblate spheroids and packing models have been developed which define the grain contact and pore spaces where electrolyte may be contained.

If the grains are solid, as glass spheres, and contain no electrically-conductive medium, the resistance characteristics of the material will assume a different appearance from that of the permeable-grain material in which the grains themselves or aggregates formed from a number of grains contain the conductive media. Thus, separate "equivalent circuits" may be derived for clays and sands, embodying the electrical features of "permeable conductive grain" or "solid dielectric grain" for clays and sands, respectively. Mixture of clays and sands could, of course, generate still other characteristic "equivalent circuits" with various ratios being catalogable. These features provide useful information for classifying materials subjected to analysis by the present invention.

Other objects, features, and characteristics of the present invention as well as the methods and operation and functions of the related elements of the structure, and to the combination of parts and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

FIG. 1a is a diagrammatic representation of $R_x$, $R_y$ and $R_z$ orthogonal coordinate axes along which electrode pairs are positioned;

FIG. 2 is a diagrammatic cross-sectional view of one of the annular sensors mounted around about the exterior of the device;

FIG. 3 is a diagrammatic cross-sectional view adjacent one of the sensors;

FIG. 4 is a diagrammatic cross-sectional view shown in FIG. 3 taken along line 4—4 thereof;

FIG. 5 is a cross-section through another type of sensor extending about the periphery of the penetrometer in FIG. 1;

FIG. 6 is a diagrammatic cross-section taken through the penetrometer along line 6—6 in FIG. 5;

FIG. 7 is a diagrammatic side elevational view of an additional penetrometer structure which could be used on the penetrometer shown in FIG. 1;

FIG. 10 is a diagrammatic side elevational view of the penetrometer as set forth in FIG. 1 showing the speed regulation mechanism and telemetry system;

FIG. 11 is a diagrammatic showing of the circuitry used to collect signals transmitted by the sensors used on the penetrometer shown on FIG. 1;

FIG. 12 shows the circuitry for obtaining deceleration data via time intervals between electrode switch closures as they enter a conductive medium, and other measurements;

FIGS. 13a and 13b diagrammatically show the circuitry used in the penetrometer shown in FIG. 1;

DETAILED DESCRIPTION OF THE PREFERRED EXEMPLARY EMBODIMENTS

Figure 1:
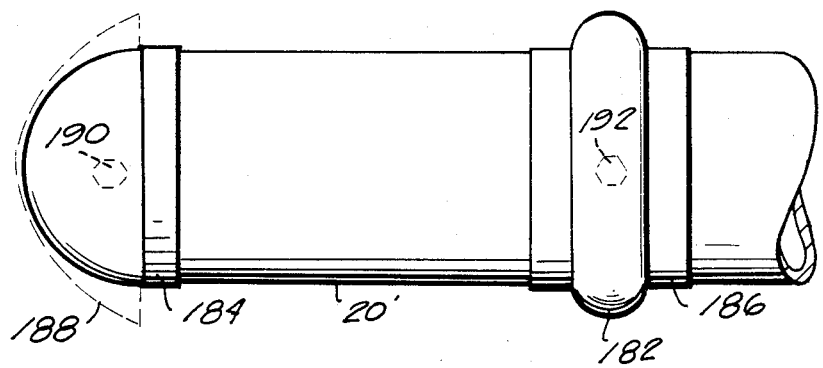
FIG. 1 is a side elevational view of a penetrometer constructed according to the present invention, partially in elevation and with portions thereof having been cut away for clarity.

Turning first to FIG. 1 it should be understood that the penetrometer according to the present invention is designed to pass through or be able to sense relative movement between it and with a medium. One type of sensing that can be performed is to sense vibrations caused by movement relative to the medium and in that regard we are interested in essentially two types of vibrations. The first constitutes low frequency perturbations where the entire vibrating body can move, on the order of fraction of 1 to approximately 10 hertz. The second type of vibration is a higher frequency vibration due to friction as the vibrating body moves against adjacent soil particles or water or other items in the medium through which it is moving with that friction being caused by interparticle forces disturbed by the penetration. The first type of vibration or low frequency vibrations can be picked up by strain gauges whereas the second higher frequency type of vibrations are generally going to be picked up by microphones with the strain gauges and microphones each being located within the device itself.

Strain gauges used herein are typically BLH, SR-foil type mounted to a cantilever beam, one-half bridge. Preferably, the input signal can be limited to 25 milliwatts with the resistance values varying from 360 to 500 ohms.

The microphones for sensing the second type of higher frequency vibrations can be similar to type MC 11 J manufactured by Shure Bros. with the microphones either being magnetic or piezoelectric.

Turning now to FIG. 1 the penetrating device or penetrometer built according to the present invention is generally indicated at 10. The front portion is indicated generally at 12 with the primary sensing portion being generally indicated at 14 and the rear control portion is generally indicated at 16.

The front portion is comprised of a penetrating body 18 mounted to the primary housing 20, which is itself preferably tubular or cylindrical in shape, via a resilient mounting member 22 in the form of a cylindrical disk and a relatively long coaxial hollow mounting stud 23a and nut 23b with screws 24 preventing nose rotation.

The rear section 16 includes fins 26 which help guide the trajectory and establish the stability of the device as it is free falling prior to penetration if that is the method of use. Fluids such as water or sea water that may be measured are excluded from housing 20 by suitable sealing means such as gaskets 28 and 30 respectively shown at the front and rear portions of housing 20. Sealing means 28 and 30, respectively, allow the introduction of conduits through the center; with respect to sealing means 30 it seals about cables 32 for linking the internal sensors within the device to suitable pickup or transmitting devices.

In those instances where the device or penetrometer is to be used in an environment where it will be passing through a portion of liquid it is of course desirable that the device be non-buoyant under all conditions where penetration will occur due to the weight of the device. It should be understood, however, that this device can be used in other environs other than free fall situations specifically if installed within a pipe or conduit carrying various types of flowing medium. In that instance, it is not necessary that the device be non-buoyant. Likewise where the device is itself to be thrust into a medium by means of a rigid shaft or other rigid deploying method which would be rigid enough to maintain the desired orientation then the buoyancy of the device is no longer a critical matter. Additionally, the device could be towed through water by a boat or other means at a fixed depth to make readings of the water or of other fluids to determine characteristics at that depth or to determine changes in bottom characteristics if the device is towed through a sediment layer above the bottom's surface.

Housing 20 is preferably not electrically conductive and accordingly can be constructed from a high impact plastic material. By constructing the housing in this fashion it will not influence any directional resistance measurements between any of the pairs of electrodes located along the length of the penetrometer as will be described more fully herein below. If it was necessary to construct housing 20 from an electrically conductive material, such as aluminum, then the electrodes would have to be insulated by suitable insulators.

The device 10 is designed so that penetrating body 18 first penetrates the medium or mediums that it will be passed through or moved past the penetrometer. The medium will be deflected and flow along so that its flow characteristics can be observed as flow moves past and around vibrating bodies positioned along the length of the device such as are indicated at 34 and 36. It should be understood that housing 20 may be of any convenient length and may have associated with it any desired number of vibrating bodies 34 and 36 so that the intended or desired function can be performed.

Figure 8:
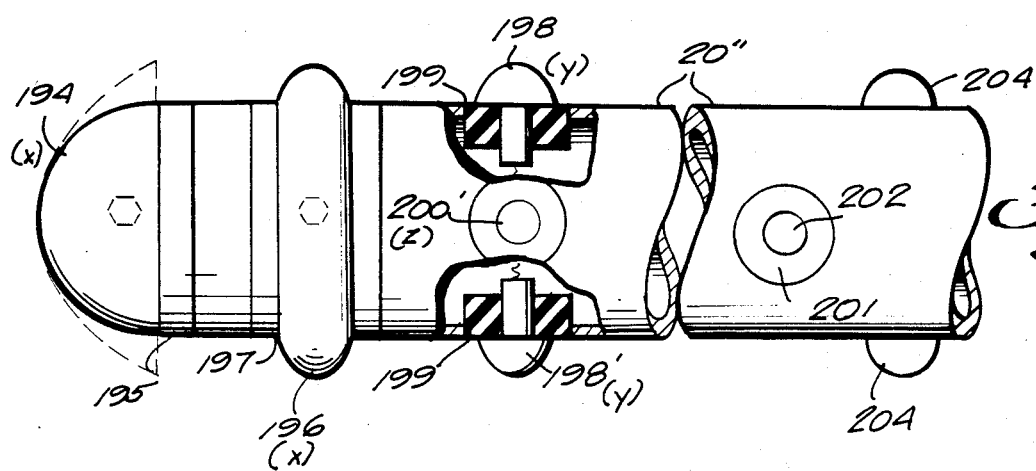
FIGS. 8 and 9 are diagrammatic side elevational views of additional sensing structures mounted on a penetrometer similar to the one shown in FIG. 1.

Penetrating body 18 may have an electrically conductive surface or may be a solid conductor thereby serving as the primary directional resistance electrode along the central axis of housing 20 or the X-axis together with electrode 38 positioned further back along housing 20 in the X-axis direction. This X direction is shown in FIG. 1a, along with the Y and Z directions which extend horizontally and at right angles to one another and in the same or different planes positioned orthogonally with respect to the X-axis. When the entire penetrating body 18 is conductive, then a plurality of companion electrodes 38 are needed along the periphery of housing 20, at that same longitudinal position and connected in parallel, so that the electric current for directional R in the X-direction will be truly in the X-direction and not at some angle as may be occasioned by single spot contact as is presently shown in FIG. 1. Further, a metallic ring is the most desired form of electrode for electrode 38 as that would extend around the housing. With reference as well to FIGS. 1a and 8, while electrodes 18 and 38 can be paired to comprise the X-direction electrodes to measure directional resistance R along the central axis of the housing ($R_X$). It should be understood that while electrodes 18 and 38 comprise one pair of X-direction electrodes which extend along the axis of the probe, any number of such $R_X$ electrode pairs can be employed and are preferably so employed, as indicated at the $R_X$ positions in FIG. 9. Electrode pairs 198 are shown on FIG. 8, for Y-direction measurements ($R_Y$), and electrode pairs 200 for Z-direction measurements ($R_Z$) can be placed at various locations on the exterior of the penetrometer. As with the $R_X$ electrode pairs, a number of $R_Y$ and $R_Z$ electrode pairs can be positioned at various points along the pentrometer, as shown by the designations $R_Y$ and $R_Z$ on FIG. 9, so that sequential readings at a number of positions can be obtained. Thus, $R_X$, $R_Y$ and $R_Z$ readings could first be obtained at or near the nose, 6–10 inches farther back than at another point 6–10 inches farther back and so on.

Each vibrating body 18, 34 and 36 is equipped with an electrical transducer 40, 42, 44 having a frequency response suitable to measure the entire spectrum of vibration of the device but particularly suited to monitor the higher frequencies, for example 18 hertz to 40,000 hertz. These frequencies arise as those bodies either displace or shear the medium being penetrated by, "scraping" past materials, therein or by disrupting interparticle forces including crushing friable materials such as soft rock or seashells or by the sound generated thereby. Sounds can also be generated by the "domino effect" that occurs when a displaced particle forces adjacent particles aside, breaks adjacent particles or otherwise creates an interparticle noise. These noises are generally aperiodic as distinct from the periodicity of a wake but by analyzing their frequency spectrum, and the power spectrum, certain materials and test conditions a catalog of materials and their responses may be obtained experimentally for reference. The outputs of transducers 40, 42 and 44, shown respectively at 41, 43 and 45, are analyzed separately, but are time-correlated with the outputs of transducers or strain gauges being described below.

Whereas transducers 40, 42 and 44 are preferably and usually of the piezelectric type such as Rochelle salts, transducers 46 for the strain gauge connected to body 18, should have a frequency response directed toward frequencies from a fraction of a hertz to a few hundred hertz, so-called strain-gages of the electrical resistance BLH type being one example. These transducers are connected mechanically to housing 20 by one strain "leg", the other "leg" being connected mechanically to the vibrating body 18, 34 and 36 respectively. Transducers 48 and 50, for bodies 34 and 36, respectively, are also of the BLH type, and are intended to monitor gross motion of these latter penetrating and tracking bodies with respect to the housing 20, the gross motions being the result of impacting large material particles, shearing, forcing large particles aside or, crushing. A signal such as a jagged burst could be due to one of the bodies encountering a lump in an otherwise consistently thin slurry.

Signal processors for the transducers and strain gages, both low-frequency and high-frequency, by blocks 52 through 60 in FIG. 11 with P representing the penetrator body 18 signals, $T_1$ representing the first following tracking body 34 signals, and $T_2$ representing the second following tracking body 36 signals. Each of these channels P, $T_1$ and $T_2$, is designed to have a signal sampler 52, an amplifier 54, a frequency distribution analyzer 56 and a frequency versus energy analyzer 58. These blocks taken as a group are typically referred to as a spectrum analyzer. Block 60 represents a "waterfall" plot of this frequency analysis over the distance penetrated and is shown in greater detail in FIG. 14.

A conventional accelerometer 70 measures changes in velocity with respect to time, dv/dt, when the penetrator encounters a deceleration in any medium. It should be understood, however, that a number of spaced electrode pairs can be provided along the exterior of housing 20. If a plurality of inertia switches are employed in connection with housing 20 with each having a different "G" rating or factor their combined signals can be observed and used in place of accelerometer 70. If they are spring loaded type, so that they recover or return to their stable state following impact, two signals can be generated, one upon impact another on their return to a stable or "at rest" state. The sequential opening and closing of such a group of inertia switches will yield deceleration data.

In electrically-conductive media, the electrode-pairs for measuring directional R may also be used to measure penetrator velocity and deceleration. For example electrode-pairs comprised of the penetrating body 18 and contact 38 and another pair comprised of contacts 72 and 74, can be considered as electrolytic switches which can actuate an oscillator (not shown) whose frequency identified a particular electrode-pair. Contacts 72 and 74 could be connected in a circuit similar to that shown for $R_z$ on FIG. 13a for contacts on electrodes 198 and 198'. Likewise other pairs of contacts could be provided at spaced apart intervals along the penetrometer body (not shown). These electrode-pairs consequently generate a series of pulses at various time intervals beginning with the first pair, 18 and 38, penetrating the conductive medium.

A first pulse will be generated at time zero. For ascertaining that the penetrator 10 has penetrated a conducting medium at the beginning of its deceleration, accelerometer 70, which may be a simple inertia switch, will provide a signal for correlation with the signal from the leading electrode pair 18 and 38. The spacing of electrode pairs along housing 20 is known hence the change in velocity over intervals between the "switching" of electrode pairs will yield deceleration information. This correlation is performed by a time interval meter 76, computer 78 and presented on a display, such as a cathode-ray tube, 80, or a chart recorder, or both.

In thin, fluid media such as water, the depth of the device may be obtained by a commercially available pressure sensor 82, such as Model 205 manufactured by Setra Systems, Inc., Natick, Mass., with electrical connections 84, whose output signal may be sent via a transducer and amplifier circuit, shown in FIG. 13a to the telemetry equipment and transmission so it can be correlated with the switch-closures of the electrode-pairs by computer 78.

Figure 13B:
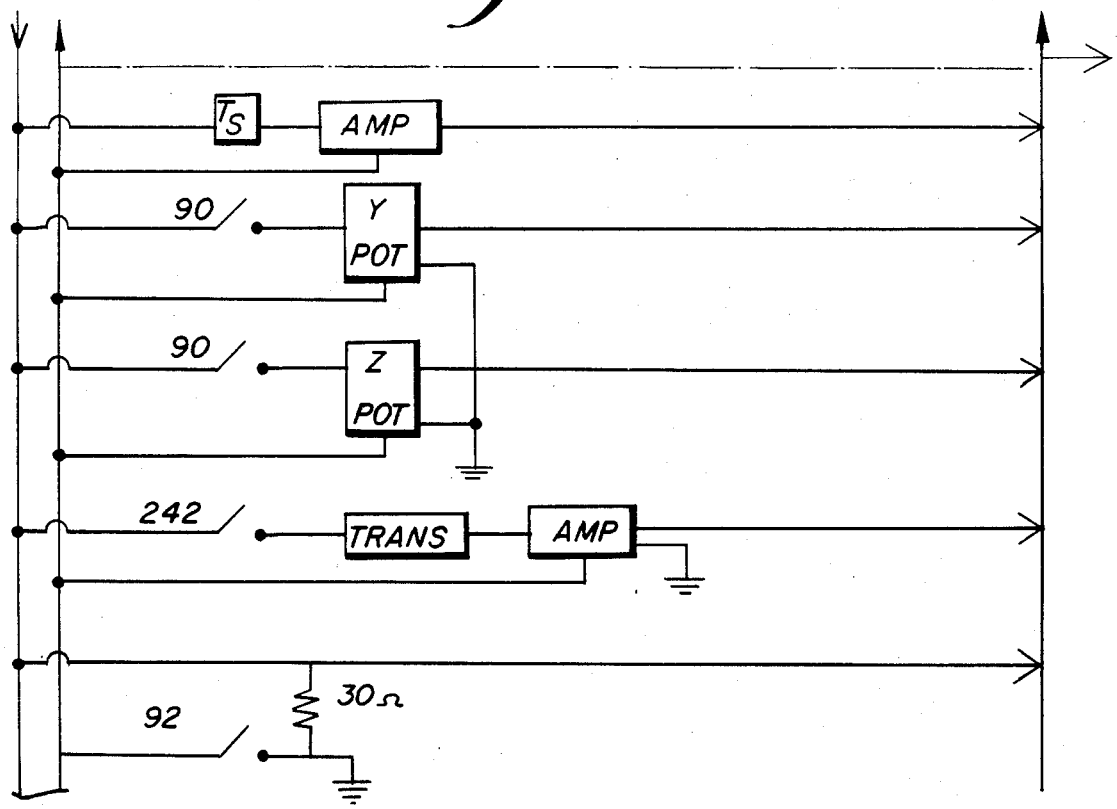

Temperature of the medium penetrated may be detected by thermal sensor 86 whose output signal is also delivered to computer 78, as shown in FIG. 12, via the circuit shown in FIG. 13b, and then delivered to data display 80 after correlation with other signals being generated, for example, the depth of the device. It may also be desirable to know the final orientation of the penetrometer 10. Accordingly, an orientation sensor 90, such as are comprised of two pendulum potentiometers manufactured by Beckman, Instruments Co., with output leads 92 can be positioned at a suitable location within the hollow interior of housing 20.

The penetrometer 10 may be designed in any length desired and may penetrate a medium for its full length or less. It may encounter a uniform medium, or a medium which is nonuniform versus depth. The media may be electrically-conductive. Certain conditions, however, may exist concerning depth of penetration and will determine how the various transducer and sensor signals are processed. Three general conditions are as follows:

(1) the penetrator 10 impacts a dense material and stops before the entire device is surrounded. In this case only the "penetrating body" 18 and possibly none of the "tracking bodies" 34 or 36 will contact the medium and deliver signals. Such an abrupt stop will be indicated by a pronounced signal from strain gauge 46, with less intense signals from strain gauges 48 and 50. The high frequency microphones 40, 42 and 44 would deliver signals but their characteristics would "fit" only "a dense material". If the device penetrated far enough to electrically connect only body 18 and electrode 38, but no other electrode-pairs the device will have impacted a dense and electrically-conductive medium such as moist soil, and a directional R signal along the X-axis is delivered. Signals would also be delivered from temperature sensor 86, orientation sensor 90, and accelerometer 70. Fluid sensor 82 normally will not be actuated.

(2) The penetrator 10 impacts a dense material and it comes to rest completely surrounded. Penetrating body 18 will deliver interparticle noise via transducer 40 and vibrations and deflection via strain-gauge transducer 46. Tracking bodies 34 and 36 likewise deliver "tracking signals" on their respective circuits for movement sensed by strain gauges 48 and 50 and for sound by microphones 42 and 44, respectively. These tracking signals are correlated with each other and "penetrator" signals from body 18. If the material is fluid enough to enter the orifice on pressure sensor 82, such a signal is delivered via output lines 84. Signals would also be delivered from temperature sensor 86, orientation sensor 90, and accelerometer 70. Additional electrode-pairs, located along housing 20, such as represented by electrodes 72 and 74, would also be "switched" producing the first time-interval signal for velocity and acceleration measurements, the aftermost electrode-pair indicating the depth to which the device has sunk. Of course, while only one representative electrode pair has been shown, other pairs could be positioned all along penetrometer 10. All such electrode-pairs would indicate directional R.

(3) The penetrator 10 impacts a material of varying density versus depth such as a body of water with sludge on the bottom. Penetrator body 18 will penetrate first delivering a signal via microphone transducers 40 and strain gauge 46. Shortly thereafter, with electrode 38, delivering a "switch-closure" at time "T zero" and a reading of directional R along the X-axis. Other electrode-pairs, such as 72-74, are then "switched" by the fluid as the penetrator enters and simultaneously deliver directional R signals corresponding to their respective axes. All of the other sensors including temperature sensor 86, orientation sensor 90 and pressure (depth) sensor 82 also deliver their respective output signals.

Figure 14:
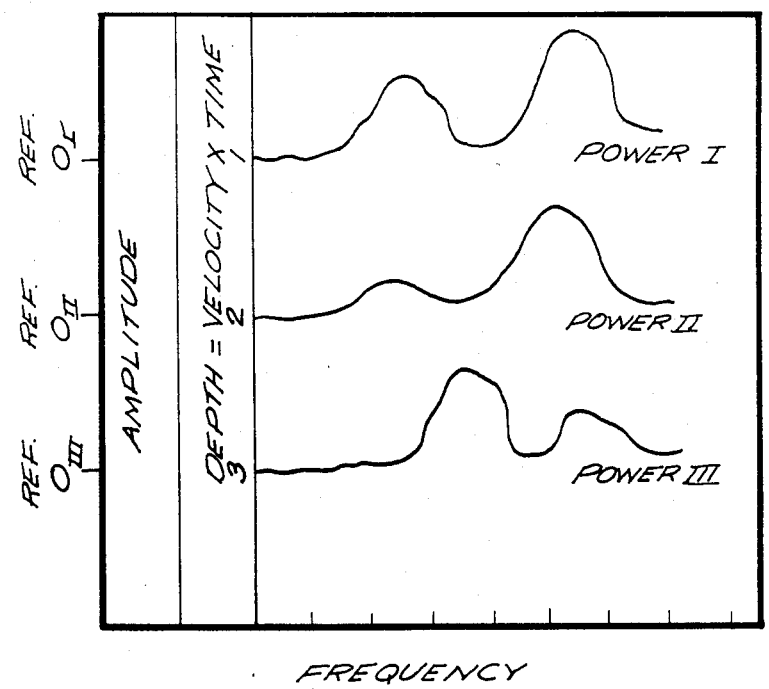
FIG. 14 diagrammatically shows the power frequency curves at three depths of a penetrating body as observed on a waterfall display.

All of the signals generated by the device will deliver several "classes" of information:

Class 1—frequency and power versus depth via the spectrum analyzer 52 through 60, presented on a "waterfall display" as an example (FIG. 14).

Figure 15:
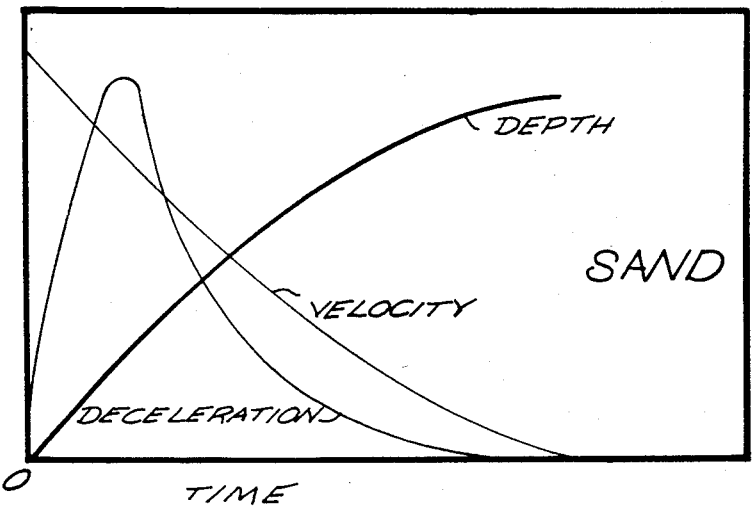
FIG. 15 shows conventional traces of a penetrometer with respect to depth and velocity and deceleration versus time in sand.

Class 2—velocity, deceleration and penetration depth information, presented separately from Class 1, most conveniently on a cathode-ray tube (FIG. 15).

Figure 16:
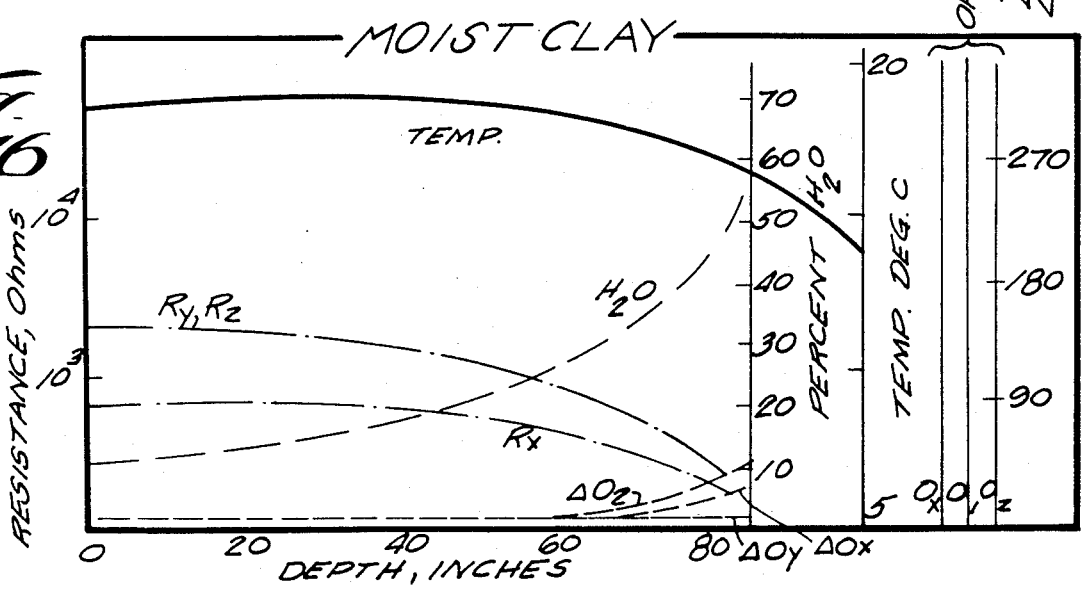
FIG. 16 shows electrical resistance in the X, Y and Z directions respectively for RX, RY and RZ, the percent of water, and temperature of the medium, and the deviation of the axis of the penetrator housing from the reference axes plotted versus depth.

Class 3—temperature, depth of penetration, percent moisture (or R, or both), and directional R, presented separately from classes 1 and 2, most conveniently on a cathode-ray tube (FIG. 16).

Class 4—Penetrator device orientation. Angular information referred to the axes of the penetrator (FIG. 1) may be furnished in digital form and recorded versus depth of the device as in FIG. 16.

The nose angle for penetrator body 18 can be determined experimentally to respond best for the materials of interest but, an included angle of sixty degrees is preferred. The peripheral bulge at the base of penetrator body 18 should not have a diameter so great as to cause, under ordinary penetration velocities, a crater to form in the material penetrated which would prevent electrical and mechanical contact of the material with contacts 38, 72 and 74, and bodies 34 and 36 or others in the series along housing 20. Typical dimensions for such a penetrating device as shown in FIG. 1 are:

Nose angle of penetrator body 18: sixty degrees
  Outside diameter of penetrator body 18: 1.25 inches
  Outside diameter of housing 20: 1.00 inch
  Outside diameter of bodies 34 and 36: 1.25 inches
  Spacing along X-axis of housing 20 of electrical contacts of about six inches. This can include contact 38 which together with nose 18a a contact pair for measuring $R_x$, with electrodes 72 and 74 comprising an electrode pair for measuring $R_z$ and between electrodes 200 and 200' comprising the electrode pair for measuring $R_y$. This spacing is also applicable to the $R_x$, $R_y$ and $R_z$ triads shown in FIG. 9.
  Housing length, six feet
  Spacing of penetrator body 18 and tracking bodies 34 and 36 etc.: nine inches.

Turning next to FIG. 2 vibrating body 34 shown in an enlarged scale. In particular, vibrating body 34 is comprised of a ring of hard material, such as nylon, which is securely mounted within a resilient seat 100 which might be made of any resilient material such as rubber with seat 100 itself being contained within an annular cavity 102 formed in and extending about the periphery of housing 20. Connected to body 34 which is in the nature of an annular rod having a round cross-section is a strain-gauge shank 104 which is connected by suitable means to both the vibrating body 34 by extending through the wall of cavity 102 so that it can be connected directly to body 34 by any convenient means such as glueing or welding, depending upon the nature of the material from which body 34 is constructed.

The other end of shank 104 is connected to the inside surface of housing 20 by any convenient means such as welding shown at 106. To assure watertight integrity of housing 20 suitable sealing 108 can be provided between that portion of shank 104 extending through the housing and housing 20.

Strain gauge 48 is secured to shank 104 where it should be understood that additional strain-gauges 110 and 112 can also be used or placed on shank 104 for purposes of obtaining additional readings. As the device penetrates the medium and the medium moves past the outer wall of 20 and member 34 that member will be moved in a certain manner as determined by the combined effects over the velocity of the device as it penetrates in the type of medium through which it is passing. The movement can be experimentally determined and catalogued for various types of mediums and that data compared with the data being generated by strain-gauge 48 so that it is possible to determine from the outputs from strain gauge 48 what type of medium is moving past body 34. If the resilient mounting 100 were not also electrically insulating it is preferred to maintain an electrical insulation and accordingly an insulation layer would need to be placed between body 34 and the resilient mounting material. It should be understood that other forms of resilient mountings, for example, springs, could also be used if desired.

Turning now to FIGS. 3 and 4 housing 20 can be comprised of an upper half 120 and lower half 122 which can be held together by a plurality of screws 124 that fit within recesses 126 provided in the sidewall of housing 20. Alternatively, as shown in FIG. 6 housing 20 with upper half 120' and lower half 122' being held together by an adhesive forming a joint 128 between the upper and lower halves.

Returning to FIGS. 3 and 4 the vibrating body 130 is shown as being constructive from metal and is mounted about housing 20 within a resilient member 132 which is in turn supported within an annular well or groove 134 formed in and extending about the circumference of housing 20. Imbedded within vibrating body 130 is an acoustic sensor or microphone 136 which is provided with an output lead 138. In addition, a strain gauge assembly, generally indicated at 140, is connected to the inside of housing 20 by means of bolt assembly 142 and includes a strain shank 144 connected between the bolt assembly 142 and vibrating body 130. A strain-gauge 146 which is provided with an output lead 148 is provided on shank 144. Both the microphone 136 and the strain gauge 146 will provide readings for low and high frequencies discussed above as shown in FIG. 3, as shank 144 is connected to vibrating body 130 by means of a hollow connecting column 150 and it is through that hollow column that output lead 138 leading to microphone 136 extends.

It should also be pointed out that vibrating member 130 is also provided with an upper half 152 and a lower half 154 which are connected together by allen screws 156 which fit into threaded holes 158.

FIGS. 5 and 6 show another embodiment for the vibrating bodies and in particular the vibrating body 160 comprised of a plastic material in the form of a ring is provided about its periphery with a metal wire or band 162 which is molded into the plastic forming the vibrating body 160. This plastic and molded structure can be molded in two halves, as mentioned above, with each half comprising the directional R electrodes while simultaneously generating drag signals.

That vibrating body 160 is again imbedded within a depression 164 formed in housing 20 and in between vibrating body 160 and depression 164 is a resilient mount 166. A strain assembly comprised of a strain shank 168 suitably connected to the inside of housing 20 and to a hollow connecting column 170 which in turn is connected to vibrating body 160 so that strain gauge 172 can be actuated by movements of the vibrating member 160 with an output being transmitted via output leads 174. The hollow connecting column 170 allows leads 176 to be connected directly through vibrating body to the metal band 162 so that the conductive periphery of body 160 can be connected to suitable output devices as will be discussed more fully hereinafter.

Figure 9:
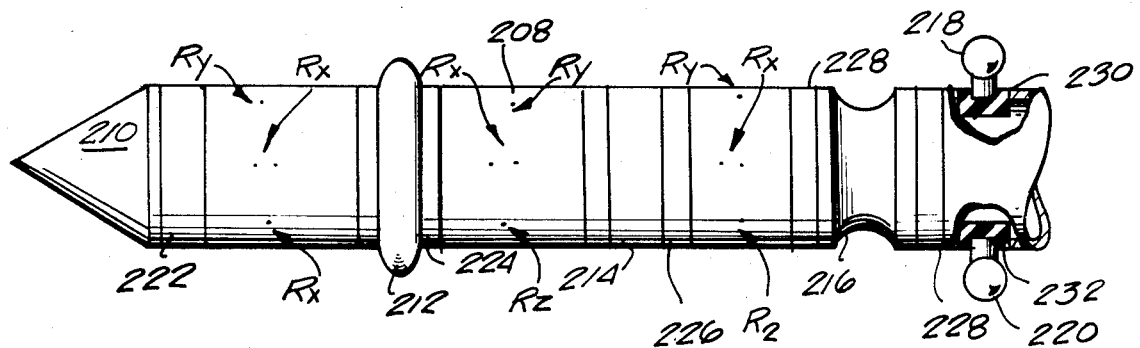

With reference to FIGS. 7, 8 and 9 further design features of this invention are shown in FIG. 7. Penetrator body 20' is shown equipped with a front penetrating surface 180 and retracking surface 182. These may be made of electrically-conductive material in which supple mechanical mountings 184 and 186 also serve as electrical insulators. Housing or body 20' is assumed to be electrically-conductive. Note that penetrating surface 180, which is represented as a rounded structure by the solid line, it should be understood that other shapes as indicated by dotted line 188 could also be used thereby more nearly simulating the diameter of retracking surface 182. That is, its diameter may exceed that of the body 20'. Being made from electrically-conductive material, body 180 and the retrack member 182 may also serve as the longitudinal resistance-measuring electrodes. Note further that if as many as four such electrodes are installed on body 20' such an array may be connected in a Wenner Resistivity Array, which has been recognized for earth investigations but which has received little investigation for sub-surface types of instruments (Geophysical Exploration, C. A. Heiland). Note further that this penetrator is equipped with acoustic monitoring transducers 190 and 192 to monitor all types of penetration signals generated by relative motion between penetrating surfaces and the medium.

Such a design as FIG. 7 is useful whenever the penetrator is to be driven into stiff media such as firm soil or sediments and the like, which may damage protruding sensors, although protruding sensors and contacting surfaces are not excluded from design and may take the form of bulges in the rigid skin of the penetrator body. The frequencies which are of interest in this instance, f3 types, generally fall outside those influenced by the loading of the nodes and antinodes of resonance of the body, hence the rigid body is a suitable design for the very stiff media.

As shown in FIG. 8, penetrator body 20'' is assumed to be metallic or otherwise electrically-conductive, with electrode-pairs 194 and 196, 198 and 198', 200 and 200' (not shown) being electrically-insulated from said body. Electrode 200' would be diametrically opposed to electrode 200. Electrodes 194 and 196 are the X-direction electrodes and would be connected in the same manner as electrodes 18 and 38 as shown in FIG. 13a; electrodes 198 and 198' are the Z-direction electrodes;

and electrodes 200 and 200' are the Y-direction electrodes. The penetrator body need not be electrically conductive and, in fact, a non-conductive body is desired from the point of view that such a non-conductive body poses less interference to the measurement of directional resistance. It should be understood that the electrodes or vibrating bodies 194, 196, 198, 198', 200 and 200' can be resiliently mounted as for example as indicated at 195, 197, 199 and 201. The Y and Z electrodes, as described above, are located in a common plane positioned perpendicularly to the central axis of housing 20", the X-axis. Either pair, however, could be moved vertically along that X-axis to another known position, such as is represented by 202 for the Y-pair or 204 for the Z-pair.

FIG. 9 shows various other configurations that the sensing surfaces may assume and in particular the various locations of $R_X$, $R_Y$ and $R_Z$ electrodes. It should be understood that while only single $R_Y$ and $R_Z$ electrodes are indicated, another contact is located directly opposite the one shown, in the same plane, with the $R_Y$ and $R_Z$ pairs being orthogonally positioned with respect to one another. The housing 208 is assumed to be electrically-conductive although as pointed out, this is not necessary. In FIG. 9 material sensing or contacting bodies 210, 212, 214, 216, 218 and 220 are shown mounted in supple insulators 222, 224, 226, 228, 230 and 232. These supple insulators, besides possibly providing electrical insulation from housing 208, provide a mounting which will permit the bodies to vibrate in accordance with the periodic flow. In general, a nose shape such as 210 may be followed by those such as 212, 218 and 220 for materials which do not leave a void which the following shape cannot contact. It is safe to assume that if a signal due to material contact is delivered from each sensor 210, 212, 214, 216, 218 and 220 as it traverses the material, this material is incapable of sustaining a void of long duration. Conversely, if this penetrator delivers signals on 210, 212, 218 and 220, but does not deliver a signal from 214 and 216, this is evidence that the penetrator is creating a cavity of approximate diameter 212, said cavity being large enough to make no contact with 214 and 216. Such conditions are possible particularly in stiff clay soils where "tracks" from other penetrating objects have been documented to persist for as long as twenty-three years.

Note also in FIG. 9 that the "knob on shaft" types of bodies 218 and 220 may be mounted along the length of the penetrator to provide flow signals as well as electrical "switch signals" signifying that that pair has entered a conductive medium or as electrodes for directional R measurements. This is also true of other types of bodies such as pairs of electrodes or bodies 212 and 214 which, when suitably spaced along the penetrator will "switch on" as they enter a conductive medium, the resolution of such pairs being dependent upon their physical spacing along the penetrator.

It should be further noted that the penetrator shown in FIG. 9 may be installed as a unit inside a conduit and be fitted with suitable electrical cables for the signals, it may be allowed to fall freely and impact the material, and deliver signals via radio telemetry, forced into the medium via a power train as from a geophysical exploration truck with suitable electrical cables conducting the signals, or other mode of utilization as conditions may require.

Turning now to FIG. 10, the device 10 is shown in an attitude where it has been released from a plane or other aerial means. As shown in dotted lines at the rear of the penetrometer 10 is a pressure releasable cover 240 which can be opened by means of aneroid latch generally indicated at 242 such as a conventional aneroid latch and elevation and water depth indicator. When cover 240 is released a parachute 244 is released. Parachute 244 is connected by means of a line 246 which is connected to a double spool 248. A second connecting line 250 is likewise connected to the inside of spool 248 so that lines 246 and 250 can play both upwardly and downwardly away from spool 248 simultaneously. Connected at the top of spool 248 is an RF transmitter 252 and a built-in power source and antenna of a conventional design capable of transmitting at frequencies varying from 215 to 235 mHz.

Parachute 244 may comprise a parachute as shown or may alternatively consist of a slowly inflating balloon which can gradually increase drag instead of causing a sudden jerk when released. The line 250 will serve to connect the RF transmitter 252 to the signals being produced by the onboard sensors and transducers in the penetrometer, for example, as are produced by the track and retracking vibrating bodies and $R_X$ $R_Y$ and $R_Z$ signals. Such cable can be supplied by Copperweld Bimetallics, Robinson Plaza II, Pittsburgh, Pa. Preferably, the cable is suitable to connect the sensors and signals coming from penetrometer 10 to the RF transmitter 252 and can also be supplied by Copperweld as for example a conductor number 24 AWG. The strain cable 246 can be approximately 200 feet long with the spool 248 having a 4½ inch outer diameter and being about 14 inches long.

The RF transmitter 252 shown located adjacent the parachute as to avoid vibration and shock problems. Likewise, with the transmitter in this portion of the device released by the aneroid switch can provide not only an elevation sensor but it can also provide a depth sensor when submerged in water and the transmitter can begin transmitting immediately upon the opening of the parachute. Further, the drag on the spool 248 causes electrical cable to be played out leaving the penetrometer 10 itself to continue virtually unimpeded toward the earth.

At the time of impact there is of course a difference in velocity between the cable which is still connected to parachute 244 and penetrometer 10 which will already have begun its penetration process. The delay in time for the cable and specifically the RF transmitter 252 to fall allows a transmission window for signals being generated during penetration by penetrometer 10. I've determined that about 5 seconds seems to be a minimum amount of time for this transmitting process to adequately transmit signals being generated during the penetration cycle.

In many instances, this will even allow for penetrometer 10 to pass through water prior to impacting in soil beneath the body of water so that the transmitter itself will not be submerged before it has transmitted the signals being generated within penetrometer 10. When impact occurs directly on land the antenna and RF transmitter following landing may still continue to transmit and this is especially true if they are caught in trees.

While cable links and the parachute can be designed to permit any desired sort of operation I have found that penetrometer impact velocity should be about 100 feet per second as I have found that this velocity will provide good penetration both through water, mud and in stiff soils producing penetration depths varying from about 4 to about 6 feet.

A nominal drop height is from about 500 feet although higher drop heights could be employed as the aneroid latch 242 can be set to deploy the parachute at any predetermined height normally 400 to 450 feet. This allows all cables to be extended to their full lengths as the penetrometer 10 is falling and allows the creation of the correct impact velocity toward the earth.

FIGS. 13a and 13b show circuitry through which signals are generated to the telemetry device via the RF transmitter 252. While these switches and signals and the generation have been discussed above, of particular importance are the signals $R_X$, $R_Y$ and $R_Z$ produced by electrode pairs as shown on FIG. 1 and 1a and on FIGS. 7, 8 and 9. The signals can be used to indicate directional resistance and may be generated by passing a locally-generated DC signal, powered by a 12-volt battery located within the penetrometer 10 and shown at the top of FIG. 13a, to a 150 hertz oscillator as indicated in the $R_X$ circuit for electrodes or contacts 18 and 38. When a circuit is completed across electrodes 18 and 38 an AC output will be generated across a 100 ohm resistor in series with electrodes 18 and 38 to AC amplifier 302, which is provided with its own DC power input, thus generating a specific output signal to the telemetry equipment specifically RF transmitter 252. This AC signal going to the amplifier is an analog of earth resistance in that direction and when properly channeled via telemetry it will produce its respective "R" direction signal for the physical position of that pair of electrodes in a given triad of R-electrodes on the pentrometer.

Signals according to $R_X$, $R_Y$ and $R_Z$ outputs which can be specifically set at, for example, 130 hertz, 160 hertz and 190 hertz, respectively, for one group or triad of electrode pairs, can be taken as the penetrometer penetrates and also when it comes to rest and can offer a great deal of information concerning the grain structure of the soil, in which the penetrometer has imbedded itself, via the infiltrating conductive electrolyte (e.g. ground water).

Similar circuits are shown for electrode pairs 198 and 198', using oscillator 304 and AC amplifier 306 as well as electrode 200 and 200' which produce an output through oscillator 308 and AC amplifier 310. While the circuit diagrams on FIG. 13a are only shown for electrode pairs 18 and 38, 198 and 198' and 200 and 200', these are representative of the circuits used for the various $R_X$, $R_Y$ and $R_Z$ electrodes or for the electrode switches such as 72 and 74.

The 12 volt battery is shown as being connected across a "power-on" switch 260 and a 1000 ohm resistor 262 to the telemetry apparatus. This circuit is not only a power-on circuit but it can also provide, via telemetry, on indication that the device has been deployed and that the power circuit is on.

Strain gauges 46, 48 and 50, as shown, as well as 146 and 172 which operate with similar circuits, are preferably of the SR4 foil type strain gauges produced by BLH Electronics, Waltham, Mass. and create output signals through low frequency amplifiers to produce signals ranging up to about 10 hertz in frequency.

The high frequency signals from acoustic transducers for microphones 40, 42 and 44, as shown, as well as 136, 190 and 192 which operate with similar circuits, also operate through separate amplifiers and deliver audio frequency signals ranging from about 10 hertz to about 5 kilohertz. The acoustic transducers or microphones preferably are a type MC11J manufactured by Shure Brothers, Inc., Evansville, Ill., but other types may be used.

The accelerometer 70 also operates through its own separate amplifier and it can be conventional piezoelectric accelerometer such as a series 5003 general purpose accelerometer manufactured by Columbia Research Laboratories, Woodlyn, Pa.

The pressure (depth) sensor 82 is connected to the telemetry system via a transducer and amplifier circuit and can generate signals corresponding to a desired range of pressures.

Temperature sensor 86 can comprise, for example, RFL model 842 distributed by the Economy Gauge and Instrument Company, Dallas, Tex., This sensor has a range from $-32$ to $+80$ degrees C. and again operates through its own amplifier.

Orientation sensor 90 can comprise two pendulum potentiometers mounted at right angles in a plane perpendicular to the axis of the penetrometer housing 20 with such a sensor being offered by Beckman Instruments Co. Both the Y and Z potentiometers which operate through the onboard battery and provide DC signals directly to the telemetry and transmitting assembly.

The aneroid switch or latch 242 can be comprised of an aneroid bellows and transducer which are connected via an amplifier to the telemetry equipment or RF transmitter 252. An analog signal corresponding to the elevation to which the pressure releasable cover is released can be generated and a pressure or depth sensor as produced by Kollsman Instrument Corp. can be used also to provide an indication as to the depth to which the sensor has travelled into water. Nose 18 and electrode 38, as shown in FIG. 1, can be correlated with the aneroid transducer to deliver a telemetered sea-level reference signal.

Inertia switch 92 can be a Model 6U0-114 manufactured by Inertia Switch, Inc., 311 W. 43rd St., NYC, rated for 10 g with a single-pole, single throw with normally open contacts. A single inertia switch can be used to detect when something hard has been hit or contacted and when penetration of the medium has begun.

It should also be understood that a plurality of these inertia switches can be used with the plurality providing a range of "g" sensitivities as, for example, ranging from about 10g to about 150g. By grouping these together and monitoring their actuation on separate telemetry channels or by individualized tone coding on one channel a deceleration profile showing deceleration versus time can be generated and their outputs can also provide data similar to that produced by an accelerometer.

By combining use of a plurality of inertia switches and a plurality of electrode pairs along the length of the penetrometer, it is possible to determine depth of penetration and that information coupled with the deceleration data from the inertia switches can provide important density data about the medium and to develop an instantaneous depth indicator as the electrode pairs short out and the inertia switches open.

Turning next to FIG. 14, this is a diagrammatic showing as to how the analysis can be carried out of the various signals generated and transmitted from the various sensors carried on board the penetrometer 10. The signals show characteristic track and retrack signatures, which when compared with known signals, can be used to indicate the type of soil conditions experienced by the penetrometer upon impact.

FIG. 15 shows curves corresponding to depth, velocity and deceleration versus time for the impacting of a potentiometer, according to the present invention, in sand.

FIG. 16 shows the curves corresponding to a directional R plot showing depth, temperature, water content and $R_Y$, $R_Z$ and $R_X$ or orientation conditions sensed by the penetrometer 10 upon impact with typical moist clays, for example, a kaolinitic soil.

While the invention has been described in connection with what is presently considered to be the most practical and preferred embodiment, it is to be understood that the invention is not to be limited to the disclosed embodiment but on the contrary, is intended to cover various modifications and equivalent arrangements included within the spirit and scope of the appended claims, which scope is to be accorded the broadest interpretation so as to encompass all such modifications and equivalent structures.

What is claimed is:

1. A probe for determining characteristics of a medium comprising an outer housing for supporting a penetration assembly, a monitoring assembly, a guide assembly and control means for controlling the impact velocity and direction, said penetration assembly including soil penetration means for allowing the probe to penetrate the soil, said monitoring assembly including a plurality of vibrating bodies positioned so as to project at least in part away from said housing so that each is vibrated a predetermined amount in response to the passage of specific mediums there past, first sensor means for sensing the vibration of each of said vibrating bodies and for generating a signal corresponding thereto, and electrode means for sensing the electrical resistance of the medium orthogonally in three separate directions.

2. A system for identifying varying types of media comprising a device for insertion into the media including first means for forming an initial track through the media and for generating and transmitting at least a first set of a plurality of signals corresponding to media characterisitics in the initial track path, and at least a second means for substantially retracking through the initial track in the media for generating and transmitting at least a second set of a plurality of signals corresponding to media characterisitics in the retrack path, and means for receiving and comparing the first set of signals with said at least a second set of signals.

3. A system as in claim 2 wherein said first set of signals includes signals corresponding to media hardness, changes in electrical resistance, shear forces and interparticle noise.

4. A system as in claim 2 or 3, wherein the signals generated during retracking at least includes signals corresponding to changes in electrical resistance, shear forces and interparticle noise.

5. A system as in claim 4 wherein the signals generated during retracking further includes signals corresponding to temperature changes of the media.

6. A system as in claim 4 wherein the signals generated during retracking further includes signals corresponding to pressure changes in the media.

7. A system as in claim 4 wherein the signals generated during retracking further includes signals corresponding to changes in the attitude of the device within the media.

8. A system as in claim 4 wherein said device further includes at least three pairs of electrodes one pair being aligned with the axis of the device, the other two pairs being positioned at right angles to one another and in at least one plane perpendicular to the axis of the device.

9. A penetrometer for establishing relative motion with a medium to determine medium characteristics along separate and known axes as insertion continues and for a predetermined period of time following insertion, said penetrometer including on board means for generating electrical signals comprising at least three separate and separated pairs of electrodes arranged around said device to generate electrical current paths in three separate orthogonal directions with each of said three separate directions being along known axes so that electrical resistance measurements can be made along said known axes.

10. A penetrometer as in claim 9 wherein the medium is the earth.

11. A penetrometer as in claim 9 wherein the medium is a fluid.

12. A penetrometer as in claim 9 wherein the medium is a solid.

13. A device for penetrating a medium and identifying varying characteristics and types of media along and adjacent the path of penetration of the device within the medium, said device comprising a housing, first means connected to said housing for forming an initial track through the media, first signal generating means for generating a first set of signals corresponding to hardness, frictional drag, changes in electrical resistance and interparticle noise along that first track, second means connected to said housing for substantially retracking through the initial track formed in the media and second signal generating means for generating a second set of signals corresponding to frictional drag, interparticle noise and changes in electrical resistance, and means for receiving the first and second sets of signals and for retransmitting such signals.

* * * * *